United States Patent [19]

Engström et al.

[11] Patent Number: 4,936,310

[45] Date of Patent: Jun. 26, 1990

[54] CATHETER FOR INTRAVASCULAR PRESSURE MEASUREMENT

[75] Inventors: Thomas Engström, Upsal; Bertil Hök, Västerås; Lars Tenerz, Uppsala, all of Sweden

[73] Assignee: Radisensor AB, Upsala, Sweden

[21] Appl. No.: 341,112

[22] Filed: Apr. 20, 1989

[30] Foreign Application Priority Data

Apr. 22, 1988 [SE] Sweden ............................. 8801517

[51] Int. Cl.⁵ .......................................... A61B 5/0215
[52] U.S. Cl. .................................. 128/673; 128/748; 73/4 R
[58] Field of Search ............................... 128/672–675, 128/748, 664–667; 73/4 R, 753, 756

[56] References Cited

U.S. PATENT DOCUMENTS 3,831,588  8/1974  Rindner ............................. 128/675
4,712,566 12/1987  Hok ................................. 128/673 X
4,718,425  1/1988  Tanaka et al. ..................... 128/673

Primary Examiner—Angela D. Sykes
Attorney, Agent, or Firm—Foley & Lardner, Schwartz, Jeffery, Schwaab, Mack, Blumenthal & Evans

[57] ABSTRACT

The invention relates to a catheter for intravascular pressure measurement. The catheter includes a leader (3) with a transducer (4). The leader is surrounded by an inner sheath (2) with a reduced partial section portion (6) and by an outer sheath (1) arranged around the inner sheath. An end closure (5) joins the outer and inner sheath to each other at the distal end of the catheter to form an outer cavity (9), intended to be pressurized by an outside pressure source, whereby the attenuated partial section sealingly surrounds the leader or transducer (4). Pressure calibration in situ is enabled with the aid of the inventive catheter.

22 Claims, 1 Drawing Sheet

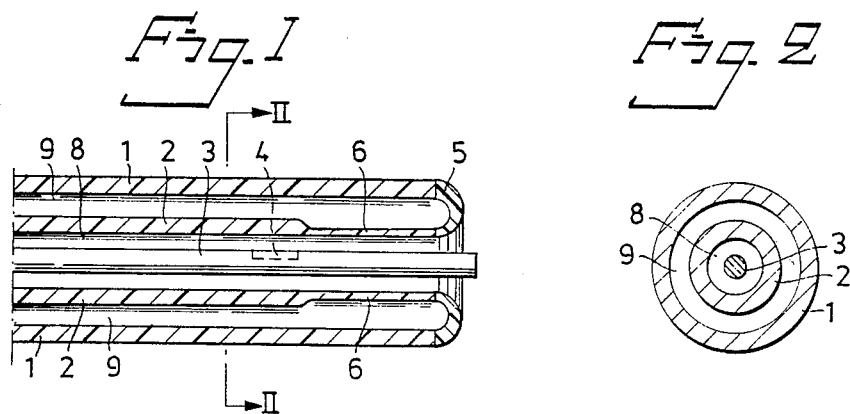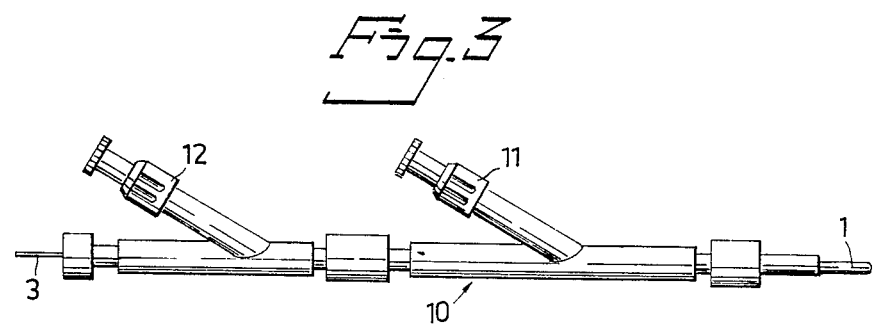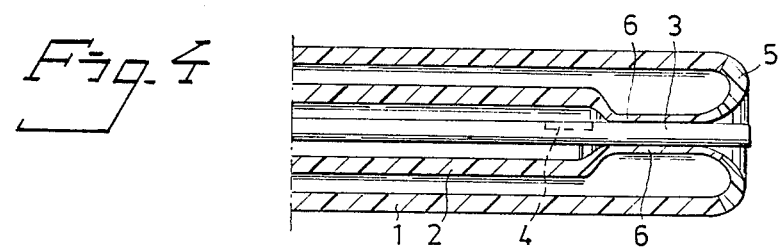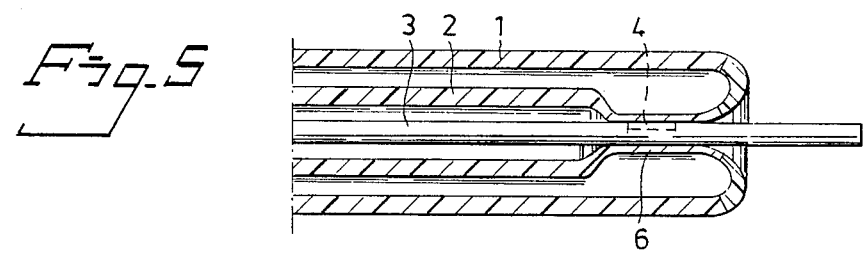

CATHETER FOR INTRAVASCULAR PRESSURE MEASUREMENT

BACKGROUND OF THE INVENTION

1. Field of the Invention

The present invention relates to a catheter for intravascular pressure measurement including an outer and an inner sheath.

2. Discussion of the Related Art

Intravascular pressure measurement involves the measurement of pressure inside a blood vessel or inside an organ to which the blood vessel leads, e.g. the heart. For this purpose, the catheter includes a so-called guide wire, known per se, which is arranged in the sheath and which is used for guiding the catheter through the blood vessel and its branches, and up to the place where pressure measurement is to be performed.

In continuous pressure measurement it is important that the pressure transducer is correctly calibrated. By this is meant that there shall be a definite relationship between the output signal of the transducer and the pressure measured by it. In electronic circuits which transmit measuring signals, signal drift often occurs due to temperature rise in the electrical components, aging of components etc. The output signal from the pressure transducer differs from transducer to transducer. For relating the output signal of the transducer, and the signal amplified by the electronic equipment, to a given pressure, e.g. 1.00 bar, the transducer is calibrated by subjecting it to this pressure of 1.00 bar, the measuring signal then being taken and the value read is then allotted to this pressure. By carrying out a series of calibrations at different pressures there is obtained a so-called calibration graph, and with this as basis the output signal of the transducer can be related to a given, definite, absolute pressure prevailing at the moment.

It is desirable to calibrate the transducer without needing to take it out of the blood vessel. The advantage with such in situ calibration is that the calibration graph is plotted with the transducer at the location of measurement. If, for example, the transducer is calibrated in a laboratory and is then transferred to an operating theatre, and lastly is inserted into the blood vessel, there is a risk that the properties of the transducer become changed due to extraneous mechanical action in the form of blows and knocks. There is also the risk that the lines connected to the transducer are disturbed or damaged. Such damage could result in false pressure measurement values. In situ calibration is also advantageous, since the pressure transducer does not need to be taken out of the blood vessel for calibration and subsequently reinserted in it, which is painful for the patient and is also a time-consuming procedure.

It is known to measure the pressure intravascularly using a pressure transducer which is in communication with the pressure registration apparatus, either via a liquid or an air column. The known apparatus of this kind have slow dynamic response and are sensitive to movement artefacts which limits the reliability of the pressure measurement.

In the Swedish patent documents 8500104-8, 8602836-2 and 8603304-0 there are described a pressure measurement system, a miniaturized sensor and a so-called guide wire.

SUMMARY OF THE INVENTION

The object of the present invention is to achieve a catheter for intravascular pressure measurement of the kind described above, which permits calibration in situ.

For achieving this, the catheter has the distinguishing features disclosed in the accompanying claims.

BRIEF DESCRIPTION OF THE DRAWINGS

The invention will now be described in more detail, and with reference to the accompanying drawings, where FIG. 1 is a longitudinal section of a catheter in accordance with the present invention, FIG. 2 is a cross section along the line II—II in FIG. 1, FIG. 3 is a side view of the means used for connecting the catheter of FIG. 1 to different outside pressure sources, FIG. 4 is a longitudinal section of the catheter in FIG. 1 in conjunction with pressure calibration and FIG. 5 is a cross section of the catheter in accordance with the invention in conjunction with pressure calibration carried out in a simplified manner.

DETAILED DESCRIPTION OF THE PREFERRED EMBODIMENTS

FIG. 1 illustrates a catheter in accordance with the present invention. The catheter has an outside diameter in the order of 1–2 mm and has a length of about 75–150 cm. It includes circular outer and inner sheaths 1 and 2, which are concentric. The diameter of each sheath is constant along the length of the catheter. A so-called guide wire 3 is arranged inside the inner sheath 2. The guide wire is provided with a pressure transducer 4. The Swedish patent specifications 8602836-2 and 8603304-0 are referred to for further details concerning the guide wire and pressure transducer. It is sufficient here to note that the guide wire often comprises a metal wire, outside which a spiral wire is spun to increase its torsional stiffness. The transducer often comprises a silicon wafer with a flat surface serving as a mirror. A light conducting optical fibre passes through the guide wire and has at its distal end a glass fibre which lies against a silicon diaphragm. This diaphragm actuated by the liquid pressure and will press in the glass fibre in front of the mirror surface to an extent depending on the liquid pressure acting on the diaphragm. The intensity of the reflected light is related in this way to the prevailing liquid pressure.

The distal ends of the outer and inner sheaths are joined to each other by an end closure 5. The distal end portion of the inner sheath has a portion with an attenuated partial section 6. An inner cavity 8 is formed between the guide wire and the inner sheath, and an outer cavity 9 is formed between the outer and inner sheaths. A hydraulic connection means 10 illustrated in FIG. 3 includes a first connection 11 to the inner cavity 8 and a second connection 12 to the outer cavity 9. In the illustrated embodiment, the connections 11 and 12 are so-called Luer connections. Unillustrated extraneous pressure sources are connected to each of the connections 11 and 12.

The sheaths 1 and 2 are made by a polymer material with good biocompatibility, e.g. polyethylene, polyurethane, fluoropolymer or the like. The attenuated partial section portion 6 is produced by a cutting tool or by forming the material. Alternatively, a separate material with a lower elastic modulus, e.g. silicon, latex or the like, can be used for the attenuated section portion 6. Such material then being joined to the inner sheath and enclosure by gluing, welding or the like.

When it is desired to measure the pressure in the blood vessel, the movable guide wire 3 inside the catheter is maneuvered so that it projects distance out from the catheter to the point where the pressure shall be measured. The catheter can also be withdrawn a distance, so as not to disturb the measurement. When the pressure has been measured the guide wire is withdrawn into the catheter.

Calibration is performed using one of the following two methods.

An exteriour pressure is created in the outer cavity 9 via the connection 12. Elastic extension of the attenuated section portion 6 then occurs and the catheter will be subjected to a change in shape, which is illustrated in FIG. 4. The attenuated inner sheath surface 6 will expand inwardly and sealingly surround the guide wire 3. When this occurs the hydraulic communication between the pressure transducer 4 and the catheter tip is broken. The transducer in the inner cavity 8 will thus be accessible to external pressure which is applied from a unillustrated pressure source via the first connection 11. A plurality of different pressure values is allowed to act on the transducer, and the signals from the transducer corresponding to these pressures are registered for plotting the calibration graph of the transducer. After terminated calilbration the pressure in the outer cavity 9 is released and the pressure registrations can be continued by uncovering the transducer.

The second method of calibrating the catheter is simplified in relation to the above method in as far as only one outside pressure source is required for calibration. The method is illustrated with reference to FIGS. 1 and 5. Starting from FIG. 1, the pressure transducer 4 is moved forward a distance until it is within the attenuated partial section portion 6. An outside pressure is then caused to act via the connection 12 and the outer cavity 9 so that the attenuated partial section closes around the guide wire 3 and its pressure transducer 4 in the way illustrated in FIG. 5. The pressure applied also constitutes the calibration pressure. The calibration graph, is determined by applying pressure at different values and then taking the corresponding values of the transducer signal. This embodiment requires that the attenuated partial section portion 6 has substantially greater resilience or compliance than the transducer 4 for a correct calibration to be obtained. Many different modifications of the invention are conceivable. The catheter described with reference to the Swedish patent specification 8602836-2 may have a transducer of some other kind, e.g. a piezo-resistive type. The outer and inner sheaths are illustrated as being concentric, but they can also be non-concentric. The diameters of the sheaths can be successively diminishing in a direction towards the distal end of the catheter illustrated in the Figures. Such an embodiment results in increased torsional stiffness, which facilitates the introduction of the catheter into such as blood vessel branches.

We claim:

1. A catheter for intravascular pressure measurement having a proximal end and a distal end, comprising:
    an outer and inner sheath and a leader moving in the inner sheath, wherein at least the inner sheath in a partial section portion is more elastic than the rest of the sheath;
    said sheaths being joined together at the distal end of the catheter to form an outer cavity which is connectable to an outside pressure source with the aide of a first connection at the proximal end of the catheter;
    a pressure transducer arranged at the leader; and
    said partial section portion being resilient, such that when a pressure is applied from the outside pressure source, it forms a seal around the leader.

2. Catheter as claimed in claim 1, wherein a connection arranged at the proximal end of the catheter is adapted to apply a pressure to the outer cavity formed between the inner and outer sheaths.

3. Catheter as claimed in claim 2, wherein a second connection is arranged at the proximal end of the catheter for connecting an outside pressure source to an inner cavity formed between the leader and the inner sheath.

4. Catheter as claimed in claim 3, wherein the outer and inner sheaths are joined to each other at the distal end of the catheter by an end closure.

5. Catheter as claimed in claim 2, wherein the outer and inner sheaths are joined to each other at the distal end of the catheter by an end closure.

6. Catheter as claimed in claim 1 wherein a second connection is arranged at the proximal end of the catheter for connecting an outside pressure source to an inner cavity formed between the leader and the inner sheath.

7. Catheter as claimed in claim 6, wherein the outer and inner sheaths are joined to each other at the distal end of the catheter by an end closure.

8. Catheter as claimed in claim 1 wherein the outer and inner sheaths are joined to each other at the distal end of the catheter by an end closure.

9. The catheter as claimed in claim 1, wherein said partial section portion is substantially thinner than the rest of the sheath, thereby being more elastic.

10. Catheter as claimed in claim 9, wherein the thin partial section portion of the inner sheath has a resilience which is substantially greater than the resilience of the pressure transducer.

11. Catheter as claimed in claim 10, wherein a connection arranged at the proximal end of the catheter is adapted to apply a pressure to the outer cavity formed between the inner and outer sheaths.

12. Catheter as claimed in claim 11, wherein a second connection is arranged at the proximal end of the catheter for connecting an outside pressure source to an inner cavity formed between the leader and the inner sheath.

13. Catheter as claimed in claim 12, wherein the outer and inner sheaths are joined to each other at the distal end of the catheter by an end closure.

14. Catheter as claimed in claim 11, wherein the outer and inner sheaths are joined to each other at the distal end of the catheter by an end closure.

15. Catheter as claimed in claim 10, wherein a second connection is arranged at the proximal end of the catheter for connecting an outside pressure source to an inner cavity formed between the leader and the inner sheath.

16. Catheter as claimed in claim 15, wherein the outer and inner sheaths are joined to each other at the distal end of the catheter by an end closure.

17. Catheter as claimed in claim 10, wherein the outer and inner sheaths are joined to each other at the distal end of the catheter by an end closure.

18. The catheter as claimed in claim 1, wherein said partial section portion comprises a material having a lower modulus of elasticity than the rest of the sheath.

19. The method of in situ calibration of a transducer of an intravascular pressure transducer while in a blood vessel or the like, comprising:
 (a) providing inner and outer sheaths, a movable leader positioned within the inner sheath, and a pressure transducer on the leader;
 (b) forming a portion of the inner sheath with a greater elasticity than the remainder of the inner sheath;
 (c) joining the inner and outer sheaths at a distal end of each thereby forming an outer cavity;
 (d) connecting the outer cavity to a first source of pressure;
 (e) forming a seal on said leader by applying pressure to the pressure source and attenuating the elastic portion.

20. The method of claim 19 including applying pressure from a second pressure source to a closed inner cavity between the inner sheath and the leader.

21. The method of claim 19 including applying a plurality of different pressures via the first pressure source and plotting a graph for obtaining calibration of the transducer.

22. The method of claim 19 including moving the leader within the attenuated portion to a point where the transducer is within an area sealed by the inner sheath and the leader whereby the pressure applied is the calibration pressure.

* * * * *